US009492679B2

(12) United States Patent
Schneider et al.

(10) Patent No.: US 9,492,679 B2
(45) Date of Patent: Nov. 15, 2016

(54) TRANSCRANIAL MAGNETIC STIMULATION FOR ALTERING SUSCEPTIBILITY OF TISSUE TO PHARMACEUTICALS AND RADIATION

(75) Inventors: M. Bret Schneider, Portola Valley, CA (US); Michael J. Partsch, Redwood City, CA (US)

(73) Assignee: Rio Grande Neurosciences, Inc., Santa Fe, NM (US)

( * ) Notice: Subject to any disclaimer, the term of this patent is extended or adjusted under 35 U.S.C. 154(b) by 400 days.

(21) Appl. No.: 13/808,806

(22) PCT Filed: Jul. 15, 2011

(86) PCT No.: PCT/US2011/044121
§ 371 (c)(1),
(2), (4) Date: Apr. 23, 2013

(87) PCT Pub. No.: WO2012/009603
PCT Pub. Date: Jan. 19, 2012

(65) Prior Publication Data
US 2013/0204330 A1    Aug. 8, 2013

Related U.S. Application Data

(60) Provisional application No. 61/365,025, filed on Jul. 16, 2010.

(51) Int. Cl.
*A61N 2/00* (2006.01)
*A61N 1/06* (2006.01)
*A61N 2/02* (2006.01)

(52) U.S. Cl.
CPC ............... *A61N 2/002* (2013.01); *A61N 1/06* (2013.01); *H05K 999/00* (2013.01); *A61N 2/02* (2013.01)

(58) Field of Classification Search
CPC .......... A61N 2/00; A61N 2/002; A61N 2/02; A61N 5/00; A61N 5/062; A61N 5/10; A61N 5/1001; A61N 5/1007; A61N 5/1014; A61N 5/1048; A61N 2/06; A61N 2/12; A61N 1/406
See application file for complete search history.

(56) References Cited

U.S. PATENT DOCUMENTS 3,799,164 A    3/1974  Rollins
4,134,395 A    1/1979  Davis
(Continued)

FOREIGN PATENT DOCUMENTS

DE    10242542 A1    4/2004
EP     0501048 A1    9/1992
(Continued)

OTHER PUBLICATIONS

Schneider et al.; U.S. Appl. No. 13/888,263 entitled "Transverse transcranial magnetic stimulation for improved analgesia," filed May 6, 2013.
(Continued)

*Primary Examiner* — Charles A Marmor, II
*Assistant Examiner* — Carrie R Dorna
(74) *Attorney, Agent, or Firm* — Shay Glenn LLP

(57) ABSTRACT

Described herein are methods for modulating the susceptibility of one or more target or tissue regions, and particularly one or more brain regions, to a therapeutic agent such as a drug, immune agent, compound, radiation, etc. In particular, the methods and systems described herein may include magnetic stimulation (including transcranial magnetic stimulation) of target or non-target regions to modulate the susceptibility of the one or more target or tissue regions to a therapeutic agent.

17 Claims, 1 Drawing Sheet

(56) References Cited

U.S. PATENT DOCUMENTS

| | | | |
|---|---|---|---|
| 4,690,130 A * | 9/1987 | Mirell | A61K 9/5094 600/10 |
| 4,889,526 A | 12/1989 | Rauscher et al. | |
| 5,047,005 A | 9/1991 | Cadwell | |
| 5,207,223 A | 5/1993 | Adler | |
| 5,267,938 A | 12/1993 | Konotchick | |
| 5,427,097 A | 6/1995 | Depp | |
| 5,441,495 A | 8/1995 | Liboff et al. | |
| 5,531,227 A | 7/1996 | Schneider | |
| 5,707,334 A | 1/1998 | Young | |
| 5,738,625 A | 4/1998 | Gluck | |
| 5,766,124 A | 6/1998 | Polson | |
| 5,891,034 A | 4/1999 | Bucholz | |
| 6,042,531 A | 3/2000 | Holcomb | |
| 6,132,361 A | 10/2000 | Epstein et al. | |
| 6,132,631 A | 10/2000 | Nallan et al. | |
| 6,149,577 A | 11/2000 | Bouldin et al. | |
| 6,179,770 B1 | 1/2001 | Mould | |
| 6,179,771 B1 | 1/2001 | Mueller | |
| 6,198,958 B1 | 3/2001 | Ives et al. | |
| 6,236,875 B1 | 5/2001 | Bucholz et al. | |
| 6,266,556 B1 | 7/2001 | Ives et al. | |
| 6,351,573 B1 | 2/2002 | Schneider | |
| 6,356,781 B1 | 3/2002 | Lee et al. | |
| 6,379,295 B1 | 4/2002 | Woo | |
| 6,425,852 B1 | 7/2002 | Epstein et al. | |
| 6,447,440 B1 | 9/2002 | Markoll | |
| 6,459,924 B1 | 10/2002 | Creighton et al. | |
| 6,461,289 B1 | 10/2002 | Muntermann | |
| 6,488,617 B1 | 12/2002 | Katz | |
| 6,507,751 B2 | 1/2003 | Blume et al. | |
| 6,537,197 B1 | 3/2003 | Ruohonen et al. | |
| 6,571,123 B2 | 5/2003 | Ives et al. | |
| 6,572,528 B2 | 6/2003 | Rohan et al. | |
| 6,663,556 B2 | 12/2003 | Barker | |
| 6,818,669 B2 | 11/2004 | Moskowitz et al. | |
| 6,849,040 B2 | 2/2005 | Ruohonen et al. | |
| 6,858,000 B1 | 2/2005 | Schukin et al. | |
| 6,926,659 B1 * | 8/2005 | Sandstrom | 600/9 |
| 6,972,097 B2 | 12/2005 | Yoshida et al. | |
| 7,023,311 B2 | 4/2006 | Baldwin et al. | |
| 7,087,008 B2 | 8/2006 | Fox et al. | |
| 7,088,210 B2 | 8/2006 | Day et al. | |
| 7,104,947 B2 | 9/2006 | Riehl | |
| 7,130,203 B2 | 10/2006 | Mbaye | |
| 7,141,028 B2 | 11/2006 | McNew | |
| 7,153,256 B2 | 12/2006 | Riehl et al. | |
| 7,155,284 B1 | 12/2006 | Whitehurst et al. | |
| 7,236,830 B2 | 6/2007 | Gliner | |
| 7,239,910 B2 | 7/2007 | Tanner | |
| 7,367,935 B2 | 5/2008 | Mechlenburg et al. | |
| 7,367,936 B2 | 5/2008 | Myers et al. | |
| 7,396,326 B2 | 7/2008 | Ghiron et al. | |
| 7,437,196 B2 | 10/2008 | Wyler et al. | |
| 7,483,747 B2 | 1/2009 | Gliner et al. | |
| 7,520,848 B2 | 4/2009 | Schneider et al. | |
| 7,670,838 B2 | 3/2010 | Deisseroth et al. | |
| 7,771,341 B2 | 8/2010 | Rogers | |
| 7,856,264 B2 | 12/2010 | Firlik et al. | |
| 7,904,134 B2 | 3/2011 | McIntyre et al. | |
| 8,052,591 B2 | 11/2011 | Mishelevich | |
| 8,265,910 B2 | 9/2012 | Mishelevich et al. | |
| 8,267,850 B2 | 9/2012 | Schneider et al. | |
| 2002/0022777 A1 | 2/2002 | Crieghton et al. | |
| 2002/0042563 A1 | 4/2002 | Becerra et al. | |
| 2002/0097125 A1 | 7/2002 | Davey | |
| 2003/0004392 A1 | 1/2003 | Tanner et al. | |
| 2003/0028072 A1 | 2/2003 | Fischell et al. | |
| 2003/0065243 A1 | 4/2003 | Tanner | |
| 2003/0204135 A1 | 10/2003 | Bystritsky | |
| 2004/0010177 A1 | 1/2004 | Rohan et al. | |
| 2004/0077921 A1 | 4/2004 | Becker et al. | |
| 2004/0078056 A1 | 4/2004 | Zangen et al. | |
| 2004/0156884 A1 | 8/2004 | Brown et al. | |
| 2004/0193000 A1 | 9/2004 | Riehl | |
| 2004/0193002 A1 | 9/2004 | Tanner et al. | |
| 2005/0010265 A1 | 1/2005 | Fassio et al. | |
| 2005/0033154 A1 | 2/2005 | deCharms | |
| 2005/0038313 A1 | 2/2005 | Ardizzone | |
| 2005/0046532 A1 | 3/2005 | Dodd | |
| 2005/0107655 A1 | 5/2005 | Holzner | |
| 2005/0113630 A1 | 5/2005 | Fox et al. | |
| 2005/0124848 A1 | 6/2005 | Holzner | |
| 2005/0148808 A1 | 7/2005 | Cameron et al. | |
| 2005/0154426 A1 | 7/2005 | Boveja et al. | |
| 2005/0182287 A1 | 8/2005 | Becker | |
| 2005/0182288 A1 | 8/2005 | Zabara | |
| 2005/0222625 A1 | 10/2005 | Laniado et al. | |
| 2005/0234286 A1 | 10/2005 | Riehl et al. | |
| 2005/0256539 A1 | 11/2005 | George et al. | |
| 2006/0058853 A1 | 3/2006 | Bentwich | |
| 2006/0094924 A1 | 5/2006 | Riehl et al. | |
| 2006/0106430 A1 | 5/2006 | Fowler et al. | |
| 2006/0122454 A1 | 6/2006 | Riehl et al. | |
| 2006/0122496 A1 | 6/2006 | George et al. | |
| 2006/0149337 A1 | 7/2006 | John | |
| 2006/0173274 A1 | 8/2006 | George et al. | |
| 2006/0189866 A1 | 8/2006 | Thomas et al. | |
| 2006/0199992 A1 | 9/2006 | Eisenberg et al. | |
| 2006/0218790 A1 | 10/2006 | Day et al. | |
| 2006/0287566 A1 | 12/2006 | Zangen et al. | |
| 2007/0027353 A1 | 2/2007 | Ghiron et al. | |
| 2007/0027504 A1 | 2/2007 | Barrett et al. | |
| 2007/0083074 A1 | 4/2007 | Sotiriou | |
| 2007/0100392 A1 | 5/2007 | Maschino et al. | |
| 2007/0100398 A1 | 5/2007 | Sloan | |
| 2007/0242406 A1 | 10/2007 | Annis et al. | |
| 2007/0265489 A1 | 11/2007 | Fowler et al. | |
| 2007/0293916 A1 | 12/2007 | Peterchev | |
| 2008/0033297 A1 | 2/2008 | Sliwa | |
| 2008/0058582 A1 | 3/2008 | Aho et al. | |
| 2008/0064950 A1 | 3/2008 | Ruohonen et al. | |
| 2008/0123922 A1 | 5/2008 | Gielen et al. | |
| 2008/0161636 A1 | 7/2008 | Hurme et al. | |
| 2008/0200749 A1 | 8/2008 | Zheng et al. | |
| 2008/0262287 A1 | 10/2008 | Dussau | |
| 2008/0306326 A1 | 12/2008 | Epstein | |
| 2009/0005631 A1 * | 1/2009 | Simenhaus et al. | 600/9 |
| 2009/0018384 A1 | 1/2009 | Boyden et al. | |
| 2009/0024021 A1 | 1/2009 | George et al. | |
| 2009/0099405 A1 | 4/2009 | Schneider et al. | |
| 2009/0099623 A1 | 4/2009 | Bentwich | |
| 2009/0112133 A1 | 4/2009 | Deisseroth et al. | |
| 2009/0112277 A1 | 4/2009 | Wingeier et al. | |
| 2009/0114849 A1 | 5/2009 | Schneider et al. | |
| 2009/0124848 A1 | 5/2009 | Miazga | |
| 2009/0187062 A1 | 7/2009 | Saitoh | |
| 2009/0189470 A1 | 7/2009 | McClellan | |
| 2009/0227830 A1 | 9/2009 | Pillutla et al. | |
| 2009/0234243 A1 | 9/2009 | Schneider et al. | |
| 2009/0287036 A1 * | 11/2009 | Shapiro | A61N 2/02 600/12 |
| 2010/0004500 A1 | 1/2010 | Gliner et al. | |
| 2010/0185042 A1 | 7/2010 | Schneider et al. | |
| 2010/0210894 A1 | 8/2010 | Pascual-Leone et al. | |
| 2010/0256436 A1 | 10/2010 | Partsch et al. | |
| 2010/0256438 A1 | 10/2010 | Mishelevich et al. | |
| 2010/0256439 A1 | 10/2010 | Schneider et al. | |
| 2010/0298623 A1 | 11/2010 | Mishelevich et al. | |
| 2010/0331602 A1 | 12/2010 | Mishelevich et al. | |
| 2011/0060179 A1 | 3/2011 | Aho et al. | |
| 2011/0082326 A1 | 4/2011 | Mishelevich et al. | |
| 2011/0184223 A1 | 7/2011 | Peterchev et al. | |
| 2011/0273251 A1 | 11/2011 | Mishelevich et al. | |
| 2012/0016177 A1 | 1/2012 | Mishelevich et al. | |
| 2012/0310035 A1 | 12/2012 | Schneider et al. | |
| 2013/0006039 A1 | 1/2013 | Sadler | |

(56) References Cited

U.S. PATENT DOCUMENTS

| | | |
|---|---|---|
| 2013/0096363 A1 | 4/2013 | Schneider et al. |
| 2014/0200388 A1 | 7/2014 | Schneider et al. |
| 2015/0099921 A1 | 4/2015 | Schneider |
| 2015/0133718 A1 | 5/2015 | Schneider et al. |

FOREIGN PATENT DOCUMENTS

| | | |
|---|---|---|
| EP | 0709115 A1 | 5/1996 |
| EP | 0788813 A1 | 8/1997 |
| EP | 1326681 B1 | 1/2007 |
| GB | 2271931 A | 5/1994 |
| GB | 2336544 A | 10/1999 |
| JP | 64-046479 | 2/1989 |
| JP | 5-237197 | 9/1993 |
| JP | 2003-180649 | 7/2003 |
| JP | 2003-205040 | 7/2003 |
| KR | 10-0457104 | 11/2004 |
| WO | WO 98/56302 A1 | 12/1998 |
| WO | WO 99/39769 A1 | 8/1999 |
| WO | WO 99/55421 A2 | 11/1999 |
| WO | WO 00/74777 A1 | 12/2000 |
| WO | WO 00/78267 A2 | 12/2000 |
| WO | WO 02/09811 A1 | 2/2002 |
| WO | WO 02/32504 A2 | 4/2002 |
| WO | WO 03/082405 A1 | 10/2003 |
| WO | WO 2004/087255 A1 | 10/2004 |
| WO | WO 2005/000153 A2 | 1/2005 |
| WO | WO 2006/124914 A2 | 11/2006 |
| WO | WO 2007/050592 A2 | 5/2007 |
| WO | WO 2009/033144 A2 | 3/2009 |
| WO | WO 2009/033150 A1 | 3/2009 |
| WO | WO 2009/036040 A1 | 3/2009 |
| WO | WO 2009/042863 A1 | 4/2009 |
| WO | WO 2007/130308 A2 | 11/2009 |
| WO | WO 2009/143503 A2 | 11/2009 |

OTHER PUBLICATIONS

Mishelevich et al.; U.S. Appl. No. 14/247,087 entitled "Shaped coils for transcranial magnetic stimulation," filed Apr. 7, 2014.

Antal et al.; Transcranial Direct Current Stimulation Over Somatosensory Cortex Decreases Experimentally Induced Acute Pain Perception; Clin J Pain; vol. 24, No. 1; pp. 56-63; Jan. 2008.

Avery et al.; A Controlled Study of Repetitive Transcranial Magnetic Stimulation in Medication-Resistant Major Depression; Biological Psychiatry; vol. 59; pp. 187-194; Jul. 2005.

Barker et al.; Non invasive magnetic stimulation of the human motor cortex; Lancet; vol. 1; pp. 1106-1110; May 1985.

Barker, A. T.; An introduction to the basic principles of magnetic nerve stimulation; Journal of Clinical Neurophysiology; vol. 8; No. 1; pp. 26-37; Jan. 1991.

Basser et al.; Stimulation of myelinated nerve axon by electromagnetic induction; Medical & Biological Engineering and Computing.; vol. 29; pp. 261-268; May 1991.

Bikson et al.; Transcranial Direct Current Stimulation for Major Depression: A General System for Quantifying Transcranial Electrotherapy Dosage; Current Treatment Options in Neurology; 10(5):377-385; Sep. 2008.

Blount et al.; The Influence of Thyroid and Thiouracil on Mice Exposed to Roentgen Radiation; Science; 109(2822); pp. 83-4; Jan. 28, 1949.

Bodo et al.; The role of multidrug transporters in drug availability, metabolism and toxicity; Toxicol Lett; pp. 140-141; Review; pp. 133-143; Apr. 11, 2003.

Boggioa et al.; A randomized, double-blind clinical trial on the efficacy of cortical direct current stimulation for the treatment of major depression; International Journal of Neuropsychopharmacology; 11(2): 249-254; Mar. 2008.

Bohning et al.; Mapping transcranial magnetic stimulation (TMS) fields in vivo with MRI; NeuroReport; vol. 8; No. 11; pp. 2535-2538; Jul. 28, 1997.

Buxton; Pharmacokinetics and Phamacodynamics; Goodman & Gilman's The Pharmacological Basis of Therapeutics (11th Ed.); McGraw-Hill , © 2006; pp. 1-23; pub. date Oct. 28, 2005.

Cohen et al.; Repetitive transcranial magnetic stimulation of the right dorsolateral prefrontal cortex in posttraumatic stress disorder: a double-blind, placebo-controlled study; Am J Psychiatry; 161(3):515-24; Mar. 2004.

Conca et al.; Effect of chronic repetitive transcranial magnetic stimulation on regional cerebral blood flow and regional cerebral glucose uptake in drug treatment-resistant depressives. A brief report; Neuropsychobiology; vol. 45; No. 1; pp. 27-31; Jan. 2002.

Dantec magnetic stimulation product information on MagPro X100 with MagOption; http://www.danica.nl/neuro/neuro-magnetische-stimulatoren.htm; Jan. 15, 2009.

Davey et al.; Designing transcranial magnetic stimulation systems; IEEE Transactions on Magnetics; vol. 41; No. 3; pp. 1142-1148; Mar. 2005.

Davey et al.; Modeling the effects of electrical conductivity of the head on the induced electrical field in the brain during magnetic stimulation; Clinical Neurophysiology; vol. 114; pp. 2204-2209; Jun. 2003.

Davey et al.; Prediction of magnetically induced electric fields in biologic tissue; IEEE Transactions on Biomedical Engineering; vol. 38; pp. 418-422; May 1991.

Davey et al.; Suppressing the surface field during transcranial magnetic stimulation; IEEE Transactions on Biomedical Engineering; vol. 53; No. 2; Feb. 2006; pp. 190-194.

DeRidder et al.; Transcranial magnetic stimulation for tinnitus: influence of tinnitus duration on stimulation parameter choice and maximal tinnitus suppression; Otol Neurotol.; vol. 26; No. 4; pp. 616-619; Jul. 2005.

Epstein et al.; Magnetic coil suppression of visual perception at an extracalcarine site; J. Clin. Neurophysiol; vol. 13; No. 3; pp. 247-252; May 1996.

Fecteau et al.; Diminishing risk-taking behavior by modulating activity in the prefrontal cortex: a direct current stimulation study; J Neurosci.; 27(46):12500-5; Nov. 14, 2007.

Fitzgerald et al.; Transcranial magnetic stimulation in the treatment of depression: a double-blind, placebo-controlled trial; Arch Gen Psychiatry; 60(10):1002-8; Oct. 2003.

Fregni et al.; Anodal transcranial direct current stimulation of prefrontal cortex enhances working memory; Exp Brain Res.; 166(1); pp. 23-30; Sep. 2005.

George et al.; Prefrontal Repetitive Transcranial Magnetic stimulation (rTMS) Changes Relative Perfusion Locally and Remotely; Human Psychopharmacol Clin Exp; 14(3); pp. 161-170; Apr. 1999.

George, Mark S.; Stimulating the brain; Scientific American; Sep. 2002; pp. 67-73.

Han et al.; Multichannel magnetic stimulation system design considering mutual couplings among the stimulation coils; IEEE Trans. on Biomedical Engineering; vol. 51; No. 5; pp. 812-817; May 2004.

Hayward et al.; The role of the anterior cingulate cortex in the counting stroop task; Exp Brain Res; vol. 154(3); pp. 355-358; Feb. 2004.

Hemond et al.; Transcranial magnetic stimulation in neurology: What we have learned from randomized controlled studies; Neuromodulation: Technology at the Neural Interface; vol. 10; No. 4; pp. 333-344; Oct. 2007.

Hovey, C. et al.; The new guide to magnetic stimulation; The Magstim Company Ltd.; Carmarthenshire, United Kingdom; Oct. 2003; 42 pages.

Hsu et al.; Analysis of Efficiency of Magnetic Stimulation; IEEE Transactions on Biomedical Engineering; vol. 50. No. 11; Sep. 2003; pp. 1276-1285.

Huang et al.; Theta Burst Stimulation of the Human Motor Cortex; Neuron; vol. 45; pp. 201-206; Jan. 2005.

Isenberg et al.; Low frequency rTMS stimulation of the right frontal cortex is as effective as high frequency rTMS stimulation of the left frontal cortex for antidepressant-free, treatment-resistant depressed patients; Ann Clin Psychiatry; vol. 17; No. 3; pp. 153-159; Jul.-Sep. 2005.

Kamitani et al.; A model of magnetic stimulation of neocortical neurons; Neurocomputing; vol. 38; No. 40; Jun. 2001; pp. 697-703.

(56) References Cited

OTHER PUBLICATIONS

Kandel et al.; Chapter 12: Synaptic Integration; Principles of Neural Science; Editors: Kandel, Schwartz and Jessell; 4th Edition, McGraw-Hill; pp. 208-227; Jan. 5, 2000.
Khedr et al.; Therapeutic effect of repetitive transcranial magnetic stimulation on motor function in Parkinson's disease patients; Eur J Neurol; 10(5):567-72; Sep. 2003.
Kimeldorf et al.; The effect of exercise upon the lethality of roentgen rays for rats; Science; 112(2902); pp. 175-176; Aug. 1950.
Kleinjung et al.; Transcranial magnetic stimulation: a new diagnostic and therapeutic tool for tinnitus patients; Int Tinnitus J.; 14(2):112-8; Jul./Dec. 2008.
Lang et al.; Bidirectional Modulation of Primary Visual Cortex Excitability: A Combined tDCS and rTMS Study; Investigative Ophthalmology and Visual Science; 48(12): 5782-5787; Dec. 2007.
Lang et al.; How does transcranial DC stimulation of the primary motor cortex alter regional neuronal activity in the human brain?; Eur. J. Neurosci.; vol. 22; No. 2; pp. 495-504; Jul. 2005.
Lang et al.; Preconditioning with Transcranial Direct Current Stimulation Sensitizes the Motor Cortex to Rapid-Rate Transcranial Magnetic Stimulation and Controls the Direction of After-Effects; Biol. Psychiatry; 56(9): 634-639; Nov. 1, 2004.
Lefaucheur et al.; Pain relief induced by repetitive transcranial magnetic stimulation of precentral cortex; Neuroreport; vol. 12, issue 13: pp. 2963-2965; Sep. 17, 2001.
Lefaucheur et al.; Somatotopic organization of the analgesic effects of motor cortex rTMS in neuropathic pain; Neurology; vol. 67, No. 11: pp. 1998-2004; Dec. 12, 2006.
Lefaucheur, Jean-Pascal; Use of repetitive transcranial magnetic stimulation in pain relief; Expert Rev Neurother; vol. 8, No. 5: pp. 799-808; May 2008.
Lemaire et al.; Influence of blood components on the tissue uptake indices of cyclosporin in rats; J Pharmacol Exp Ther; 244(2); pp. 740-743; Feb. 1988.
Levkovitz et al.; A randomized controlled feasibility and safety study of deep transcranial magnetic stimulation; Clin. Neurophysiol.; vol. 118(12); pp. 2730-2744; Dec. 2007.
Li et al.; Antidepressant mechanism of add-on repetitive transcranial magnetic stimulation in medication-resistant depression using cerebral glucose metabolism; J Affect Disord; 127(1-3); pp. 219-229; Dec. 2010.
Lin et al.; Magnetic coil design considerations for functional magnetic stimulation; IEEE Trans. on Biomedical Eng.; vol. 47; No. 5; pp. 600-610; May 2000.
Magstim Website: http://www.magstim.com/magneticstimulators/magstimacc/12494.html (printed Mar. 23, 2010).
Mansur et al.; A sham stimulation-controlled trial of rTMS of the unaffected hemisphere in stroke patients; Neurology; 64(10):1802-1804; May 24, 2005.
Martin et al.; Transcranial magnetic stimulation for treating depression; Cochrane Review; (In (eds.): The Cochrane Library. Oxford: Update Software: The Cochrane Library. Oxford: Update Software.) (year of publication is sufficiently earlier than the effective U.S. filing and any foreign priority date) 2002.
Mayberg et al.; Deep brain stimulation for treatment-resistant depression; Neuron; vol. 45; pp. 651-660; Mar. 2005.
Miranda et al.; The Electric Field Induced in the Brain by Magnetic Stimulation: A 3-D Finite-Element Analysis of the Effects of Tissue Heterogeneity and Anisotropy; IEEE Transactions on Biomedical Engineering; vol. 50; No. 9; Sep. 2003; pp. 1074-1085.
Nadeem et al.; Computation of electric and magnetic stimulation in human head using the 3-D impedance method; IEEE Trans on Biomedical Eng; vol. 50; No. 7; pp. 900-907; Jul. 2003.
Nitsche et al.; Excitability changes induced in the human motor cortex by weak transcranial direct current stimulation; Journal of Physiology; 527(3):633-639; Sep. 15, 2000.
Ohnishi et al.; rCBF changes elicited by rTMS over DLPFC in humans; Advances in Clinical Neurophysiology (Suppl to Clin Neurophysiol.; vol. 57); Chapter 76; pp. 715-720; Dec. 2004.

O'Reardon et al.; Efficacy and safety of transcranial magnetic stimulation in the acute treatment of major depression: a multisite randomized controlled trial; Biol Psychiatry; 62(11):1208-16; Dec. 1, 2007.
Paton et al.; Vascular-brain signaling in hypertension: role of angiotensin II and nitric oxide; Curr. Hypertens Rep; vol. 9; No. 3; pp. 242-247; Jun. 2007.
Ragert et al.; Improvement of spatial tactile acuity by transcranial direct current stimulation; Clin. Neurophysiol.; 119(4):805-11; Apr. 2008 (author manuscript).
Roizenblatt et al.; Site-specific Effects of Transcranial Direct Current Stimulation on Sleep and Pain in Fibromyalgia: A Randomized, Sham-controlled study; Pain Practice; 7(4): 297-306; Dec. 7, 2007.
Rossini et al.; Transcranial magnetic stimulation: Diagnostic, therapeutic, and research potential; Neurology; vol. 68, No. 7: pp. 484-488; Feb. 13, 2007.
Roth et al.; A coil design for transcranial magnetic stimulation of adeep brain regions; J. Clin. Neurophysiology; vol. 19; No. 4; Aug. 2002; pp. 361-370.
Rubin et al.; Radiosensitivity and radioresistance of tumors; Clinical Radiation Pathology; WB Saunders; Ch. 24, pp. 894-933; Jun. 1968.
Rubin et al.; The Modification of Radiation Response; Clinical Radiation Pathology; WB Saunders; Ch. 26, pp. 973-1008; Jun. 1968.
Ruohonen et al.; (Chapter 2); Magnetic stimulation in clinical neurophysiology; Second Ed.; Ed. Elsevier Inc.; pp. 17-30; Feb. 28, 2005.
Ruohonen et al.; Focusing and targeting of magnetic brain stimulation using multiple coils; Medical & Biological Engineering and Computing; vol. 35; pp. 297-301; May 1998.
Ruohonen et al.; Theory of Multichannel Magnetic Stimulation: Toward Functional Neuromuscular Rehabilitation; IEEE Transactions on Biomedical Engineering; vol. 46; No. 6; pp. 646-651; Jun. 1999.
Ruohonen, J.; Transcranial magnetic stimulation: modelling and new techniques; (doctoral dissertation); Helsinki Univ. of Tech.; Dept. of Eng. Physics and Mathematics; Espoo, Finland; Dec. 1998.
Sackheim, H. A.; Commentary: Magnetic stimulation therapy and ECT; Convulsive Therapy; vol. 10; No. 4; Dec. 1994; pp. 255-285.
Sekino et al.; Comparison of current distributions in electroconvulsive therapy and transcranial magnetic stimulation; J. of Applied Physics; vol. 91; No. 10; pp. 8730-8732; May 15, 2002.
Smith et al.; Effect of thyroid hormone on radiation lethality; Am J Physiol; 165 (3); pp. 639-650; Jun. 1951.
Sparing et al.; Enhancing language performance with non-invasive brain stimulation R A transcranial direct current stimulation study in healthy humans; Neuropsychologia; 46(1): 261-268; Jan. 15, 2008.
Speer et al.; Opposite effects of high and low frequency rTMS on regional brain activity in depressed patients; Biol Psychiatry; 48(12); pp. 1133-1141; Dec. 15, 2000.
Speer et al.; Opposite effects of high and low frequency rTMS on regional brain activity in depressed patients; Biol. Psychiatry; vol. 48; No. 12; pp. 1133-1141; Dec. 15, 2000.
Takano et al.; Short-term modulation of regional excitability and blood flow in human motor cortex following rapid-rate transcranial magnetic stimulation; Neuroimage; vol. 23; No. 3; pp. 849-859; Nov. 2004.
Theodore et al.; Transcranial magnetic stimulation for the treatment of seizures: a controlled study; Neurology; 59(4):560-2; Aug. 27, 2002.
Traad, Monique; A Quantitative Positioning Device for Transcranial Magnetic Stimulation; Engineering in Medicine and Biology Society; 1990; Proceedings of the 12th Annual Int'l Conf. of the IEEE; Philadelphia, PA; p. 2246; Nov. 1-4, 1990.
Ueno et al.; Localized stimulation of neural tissues in the brain by means of a paired configuration of time-varying magnetic fields; J. Appl. Phys.; vol. 64; No. 10; pp. 5862-5864; Nov. 15, 1988.
Ueno; Individual differences in radio sensitivity of mice correlated with their metabolic rate; Acta Radiol Ther Phys Biol; 10(4); pp. 427-432; Aug. 1971.

(56) References Cited

OTHER PUBLICATIONS

Vayssettes-Courchay et al.; Role of the nucleus tractus solitarii and the rostral depressive area in the sympatholytic effect of 8-hydroxy-2-(di-n-propylamino)tetralin in the cat; Eur. J. Pharmacol.; vol. 242; No. 1; pp. 37-45; Sep. 21, 1993.

Wagner et al.; Three-dimensional head model simulation of transcranial magnetic stimulation; IEEE Trans. on Biomedical Engineering; vol. 51; No. 9; pp. 1586-1598; Sep. 2004.

Wagner et al.; Transcranial direct current stimulation: A computer-based human model study; NeuroImage; vol. 35; issue 3; Apr. 15, 2007; pp. 1113-1124.

Waki et al.; Junctional adhesion molecule-1 is upregulated in spontaneously hypertensive rats: evidence for a prohypertensive role within the brain stem; Hypertension; vol. 49; No. 6; pp. 1321-1327; Jun. 2007.

Wasan et al.; Lipid transfer protein I facilitated transfer of cyclosporine from low- to high-density lipoproteins is only partially dependent on its cholesteryl ester transfer activity; J Pharmacol Exp Ther; 284(2); pp. 599-605; Feb. 1998.

Wasserman et al.; Therapeutic application of repetitive magnetic stimulation: a review; Clinical Neurophysiology; vol. 112; pp. 1367-1377; Apr. 2001.

Wasserman, E. M.; Risk and safety of repetitive transcranial magnetic stimulation: report and suggested guidelines from the International Workshop on the Safety of Repetitive Transcranial Magnetic Stimulation, Jun. 5-7, 1996; Electro-encephalography and Clinical Neurophysiology; vol. 108; pp. 1-16; Jan. 1998.

Xiao et al.; Magnetic Nanocomposite Paste: An Ideal High- $\mu$, k and Q Nanomaterial for Embedded Inductors in High Frequency Electronic Appls.; Proceedings of the 9th World Multiconference on Systemics, Cybernetics and Informatics; Orlando, FL; Jul. 10-13, 2005.

Yang et al.; 3D Realistic Head Model Simulation Based on Transcranial Magnetic Stimulation; Conf Proc IEEE Eng Med Biol Soc.; vol. Suppl.; Aug. 30-Sep. 3, 2006; 4 pages.

Yu et al.; Pathogenesis of normal-appearing white matter damage in neuromyelitis optica: diffusion-tensor MR imaging; Radiology; vol. 246, No. 1: pp. 222-228; Jan. 2008.

Zanette et al.; The effect of repetitive transcranial magnetic stimulation on motor performance, fatigue and quality of life in amyotrophic lateral sclerosis; J Neurol Sci.; 270(1-2):18-22; Jul. 15, 2008.

Zheng et al. High-frequency rTMS Treatment Increases Left Prefrontal Myo-Inositol in Young Patients with Treatment-Resistant Depression; Prog Neuropsychopharmacol Biol Psychiatry; 34(7); pp. 1189-1195; Oct. 1, 2010.

Mishelevich et al.; U.S. Appl. No. 12/680,912 "Transcranial magnetic stimulation with protection of magnet-adjacent structures," filed Mar. 31, 2010.

Schneider et al.; U.S. Appl. No. 12/838,299 entitled "Transcranial magnetic stimulation field shaping," filed Jul. 16, 2010.

Schneider et al.; U.S. Appl. No. 12/912,650 entitled "Sub-motor-threshold stimulation of deep brain targets using transcranial magnetic stimulation," filed Oct. 26, 2010.

Mishelevich et al.; U.S. Appl. No. 12/990,235 entitled "Transcranial magnetic stimulation by enhanced magnetic field perturbations," filed Oct. 29, 2010.

Schneider, M. Bret .; U.S. Appl. No. 13/169,967 entitled "Enhanced Spatial Summation for Deep-Brain Transcranial Magnetic Stimulation," filed Jun. 27, 2011.

Schneider et al.; U.S. Appl. No. 13/877,428 entitled "Transverse transcranial magnetic stimulation coil placement for improved analgesia," filed Apr. 2, 2013.

Alzheimer's Association; Changing the trajectory of alzheimer's disease: a national imperative; Washington, D.C.; May 19, 2010; retrieved from the internet on Nov. 13, 2014 (http://www.alz.org/documents_custom/trajectory.pdf).

American Heart Association; Heart disease and stroke statistics—2009 update: a report from the american heart association statistics committee and stroke statistics subcommittee; Circulation; 119(3); e21-181; Jan. 27, 2009.

Bentwich et al.; Beneficial effect of repetitive transcranial magnetic stimulation combined with cognitive training for the treatment of alzheimer's disease: a proof of concept study; J. Neural. Tranm.; 118(3); pp. 463-471; Mar. 2011.

Brainsway; Brainsway reports positive final results in alzheimer's trial; 2 pages; Jan. 21, 2015; retrieved from the internet (http://www.evaluategroup.com/Universal/View.aspx?type=Story&id=357486).

Centers for Disease Control and Prevention; Prevalence of stroke-United States, 2005; MMWR Morb. Mortal. Wkly rep.; 56(19); pp. 469-474; May 18, 2007.

Cotelli et al.; Improved language performance in alzheimer disease following brain stimulation; J. Neurol Neurosurg. Pschiatry; 82(7); pp. 794-797; Jul. 2011.

Ireael Hayom; Israel's neuronix offers new alzheimer's treatment; 2 pages; Nov. 5, 2012; retrieved from the internet (http://www.israelhayom/site/newsletter_article.php?id=6303).

Kessler et al.; Prevalence, severity, and comorbidity of 12-month DSM-IV disorders in the national comorbidity survey replication (NCS-R); Arch. Gen. Psychiatry; 62(6); pp. 617-627; Jun. 2005.

Koob et al.; Neurocircultry of addiction; Neuropsychopharmacology; 35(1); pp. 217-238; Jan. 2010.

Laxton et al.; A phase I trial of deep brain stimulation of memory circuits in alzheimer's disease; Ann. Neurol.; 68(4); pp. 521-534; Oct. 2010.

SAMHSA (Center for Behavioral Health Statistics and Quality); National survey on drug use and health 2009 and 2010; 2010 Tables: Adult Mental Health; 80 pages; Nov. 14, 2014; retrieved from the internet (http://www.samhsa.gov/data/NSDUH/2k10MH_Findings/2k10MH_DTables/Sect1peMHtabs.htm#TopOfPage).

Schott et al.; Fiber density between rhinal cortex and activated ventrolateral prefrontal regions predicts episodic memory performance in humans; Proc. Natl. Acad. Sci. USA; 108(13); pp. 5408-5413; Mar. 29, 2011.

Andrade et al.; Cross-national comparisons of the prevalences and correlates of mental disorders; Bull. World Health Organ.; 78(4); pp. 413-425; (year of pub. sufficiently earlier than effective US filed and any foreign priority date) 2000.

Schneider et al.; U.S. Appl. No. 14/852,415 entitled "Transcranial magnetic stimulation for improved analgesia," filed Sep. 11, 2015.

\* cited by examiner

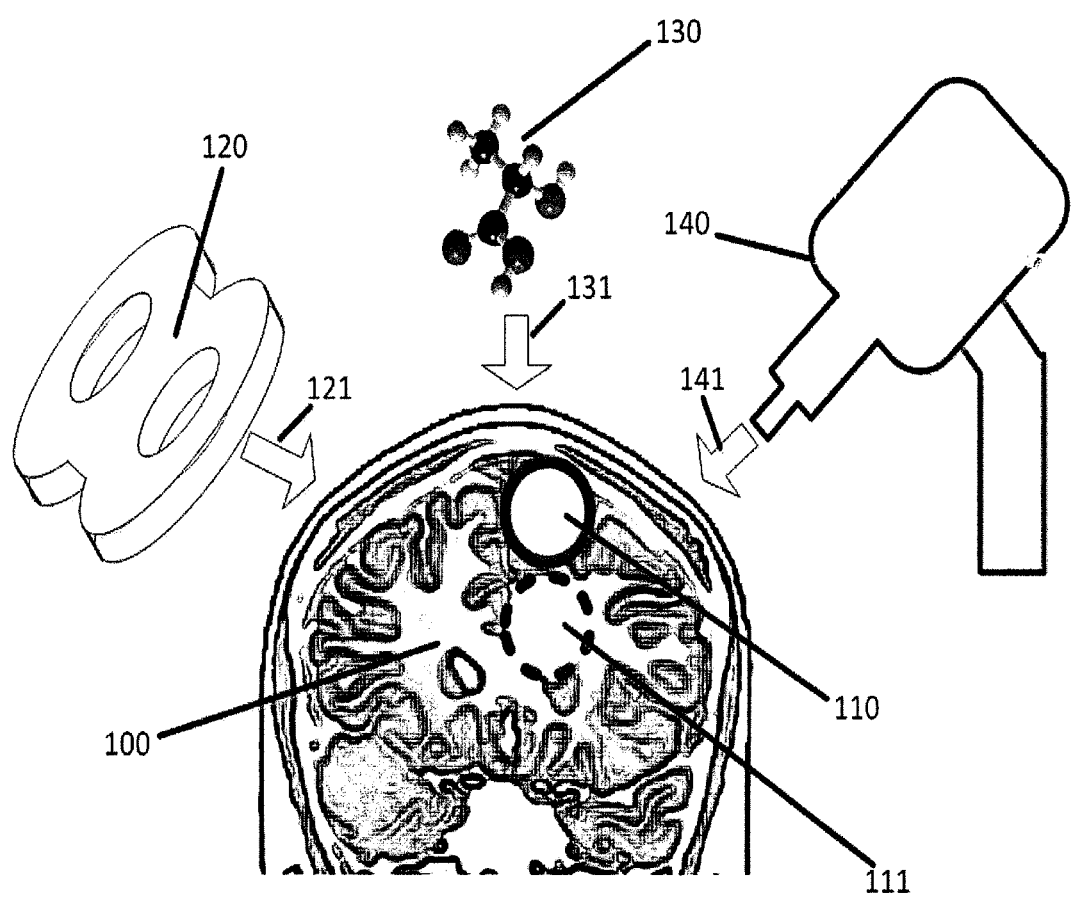

TRANSCRANIAL MAGNETIC STIMULATION FOR ALTERING SUSCEPTIBILITY OF TISSUE TO PHARMACEUTICALS AND RADIATION

CROSS REFERENCE TO RELATED APPLICATIONS

This patent application claims priority to provisional patent application Ser. No. 61/365,025, titled "TRANSCRANIAL MAGNETIC STIMULATION FOR ALTERING SUSCEPTIBILITY OF TISSUE TO PHARMACEUTICALS AND RADIATION," filed on Jul. 16, 2010.

This patent application may be related to one or more of the following patents and pending patent applications (US and PCT applications), each of which is herein incorporated by reference in its entirety: U.S. Pat. No. 7,520,848, titled "ROBOTIC APPARATUS FOR TARGETING AND PRODUCING DEEP, FOCUSED TRANSCRANIAL MAGNETIC STIMULATION", issued on Apr. 21, 2009; U.S. patent application Ser. No. 12/402,404, titled "ROBOTIC APPARATUS FOR TARGETING AND PRODUCING DEEP, FOCUSED TRANSCRANIAL MAGNETIC STIMULATION", filed on Mar. 11, 2009; U.S. patent application Ser. No. 11/429,504, titled "TRAJECTORY-BASED DEEP-BRAIN STEREOTACTIC TRANSCRANIAL MAGNETIC STIMULATION", filed on May 5, 2006; U.S. patent application Ser. No. 12/669,882, titled "DEVICE AND METHOD FOR TREATING HYPERTENSION VIA NON-INVASIVE NEUROMODULATION", filed on Jan. 20, 2010; U.S. patent application Ser. No. 12/671,260, titled "GANTRY AND SWITCHES FOR POSITION-BASED TRIGGERING OF TMS PULSES IN MOVING COILS", filed on Jan. 29, 2010; U.S. patent application Ser. No. 12/670,938, titled "FIRING PATTERNS FOR DEEP BRAIN TRANSCRANIAL MAGNETIC STIMULATION", filed on Jan. 27, 2010; U.S. patent application Ser. No. 12/677,220, titled "FOCUSED MAGNETIC FIELDS", filed on Mar. 9, 2010; PCT Application No. PCT/US2008/077851, titled "SYSTEMS AND METHODS FOR COOLING ELECTROMAGNETS FOR TRANSCRANIAL MAGNETIC STIMULATION", filed on Sep. 26, 2008; PCT Application No. PCT/US2008/081048, titled "INTRA-SESSION CONTROL OF TRANSCRANIAL MAGNETIC STIMULATION", filed on Oct. 24, 2008; U.S. patent application Ser. No. 12/324,227, titled "TRANSCRANIAL MAGNETIC STIMULATION OF DEEP BRAIN TARGETS", filed on Nov. 26, 2008; PCT Application No. PCT/US2009/045109, titled "TRANSCRANIAL MAGNETIC STIMULATION BY ENHANCED MAGNETIC FIELD PERTURBATIONS", filed on May 26, 2009; U.S. patent application Ser. No. 12/185,544, titled "MONOPHASIC MULTI-COIL ARRAYS FOR TRANSCRANIAL MAGNETIC STIMULATION", filed on Aug. 4, 2008; U.S. patent application Ser. No. 12/701,395, titled "CONTROL AND COORDINATION OF TRANSCRANIAL MAGNETIC STIMULATION ELECTROMAGNETS FOR MODULATION OF DEEP BRAIN TARGETS", filed on Feb. 5, 2010; and PCT Application No. PCT/US2010/020324, titled "SHAPED COILS FOR TRANSCRANIAL MAGNETIC STIMULATION", filed on Jan. 7, 2010.

INCORPORATION BY REFERENCE

All publications, including patents and patent applications, mentioned in this specification are herein incorporated by reference in their entirety to the same extent as if each individual publication was specifically and individually indicated to be incorporated by reference.

FIELD OF THE INVENTION

Described herein are systems and methods for treating tissue, such as neuronal tissue and particularly brain tissue using Transcranial Magnetic Stimulation (TMS) to modulate the susceptibility of the target tissue to pharmaceutical and/or radiation treatment.

BACKGROUND OF THE INVENTION

Treatment of disease, pain and medical disorders using drugs and/or ionizing radiation (e.g., pharmacotherapy) may be more effective and may have fewer or less severe side-effects when that available of the drug/radiation treatment to a targeted tissue (for example a tumor or other diseased area of the body) is enhanced and/or where availability of the drug/radiation to non-targeted tissue is minimized. For example, radiation therapy and stereotactic radio surgery may be made more effective and less damaging to non-targeted tissues if targeted tissues such as tumors are radio sensitized prior to treatment, or when surrounding non-targeted tissue are radio protected.

The availability of a pharmaceutical to a given tissue in the body is determined by several factors including the concentration of the drug in the systemic circulation, plasma protein binding, the solubility of the drug within that organ, histological/anatomical barriers, the size of the tissue, and the blood flow or perfusion of that tissue. Specifically, the better perfused a tissue, the more drug is brought to a tissue per unit time. (e.g., Brunto et al, Moskowitz et al).

The sensitivity of a given tissue in the body to the effects of ionizing radiation is determined by several factors including the rate of cellular division, the state of differentiation of the cells, the degree of nourishment to those cells including blood perfusion, and the metabolic rate of that tissue (e.g., Rubin and Casarett). Better-nourished tumors are paradoxically more radiosensitive than those that are marginally nourished, although such tissue may also be better capable of carrying out repair to radiation-injured tissue. Most importantly, the higher the metabolic rate of a tissue, the more radiosensitive it is (Ueno 1971, Kimeldorf et al 1950, Smith et al 1951, Blount et al 1949, Rubin et al 1968).

Magnetic stimulation is a known method by which the perfusion of and the metabolic rate of targeted tissue may be alternatively increased or decreased (Zheng et al, Li et al, George et al, Speer et al).

The methods and systems described herein apply targeted magnetic stimulation to change the perfusion and metabolic rate of tissue, thereby making selected tissue more susceptible to the effects of a drug or ionizing radiation, and for making non-targeted tissue less susceptible to such effects.

References that my help provide context and background include, and may be referred to as indicated above include:

Ueno Y. Individual differences in radio sensitivity of mice correlated with their metabolic rate.

Acta Radiol Ther Phys Biol. 1971 August; 10(4):427-32. No abstract available.

Kimeldorf D J, Jones D C, Fishler M C. The effect of exercise upon the lethality of roentgen rays for rats. Science. 1950 Aug. 11; 112(2902):175-6.

Smith W W, Smith F. Effect of thyroid hormone on radiation lethality. Science. 1949 Jan. 28; 109(2822):83-4. Am J Physiol. 1951 June; 165(3):639-50.

Blount H C Jr, Smith W W. The Influence of Thyroid and Thiouracil on Mice Exposed to Roentgen Radiation. Science. 1949 Jan. 28; 109(2822):83-4.

Rubin P, Casarett G W. Clinical Radiation Pathology (Philadelphia: W B Saunders. 1968

Lemaire M, Pardridge W M, Chaudhuri G. Influence of blood components on the tissue uptake indices of cyclosporin in rats. J Pharmacol Exp Ther. 1988 February; 244(2):740-3.

Bodó A, Bakos E, Szeri F, Váradi A, Sarkadi B. The role of multidrug transporters in drug availability, metabolism and toxicity. Toxicol Lett. 2003 Apr. 11; 140-141:133-43. Review.

Wasan K M, Ramaswamy M, Wong W, Pritchard P H. Lipid transfer protein I facilitated transfer of cyclosporine from low- to high-density lipoproteins is only partially dependent on its cholesteryl ester transfer activity. J Pharmacol Exp Ther. 1998 February; 284(2):599-605.

Brunton L L, Lazo J S, Parker K L. Goodman & Gilman's The Pharmacological Basis of Therapeutics. 11$^{th}$ Edition. 2006 McGraw-Hill Companies Inc.

Moskowitz M, Liao J, Omstead M N, Ron E. Increasing cerebral bioavailability of drugs. U.S. Pat. No. 6,818,669

George M S, Stallings L E, Speer A M, Nahas Z, Spicer K M, Vincent D J, Bohning D E, Cheng K T, Molloy, M, Teneback C C, Risch S C. Prefrontal Repetitive Transcranial Magnetic stiulation (rTMS) Changes Relative Perfusion Locally and Remotely. Human Psychopharmacol Clin Exp. 14, 161-170 (1999)

Speer A M, Kimbrell T A, Wassermann E M, D Repella J, Willis M W, Herscovitch P, Post R M. Opposite effects of high and low frequency rTMS on regional brain activity in depressed patients. Biol Psychiatry. 2000 Dec. 15; 48(12): 1133-41.

Li C T, Wang S J, Hirvonen J, Hsieh J C, Bai Y M, Hong C J, Liou Y J, Su T P. Antidepressant mechanism of add-on repetitive transcranial magnetic stimulation in medication-resistant depression using cerebral glucose metabolism. J Affect Disord. 2010 Jul. 1.

Zheng H, Zhang L, Li L, Liu P, Gao J, Liu X, Zou J, Zhang Y, Liu J, Zhang Z, Li Z, Men W. High-frequency rTMS Treatment Increases Left Prefrontal Myo-Inositol in Young Patients with Treatment-Resistant Depression. Prog Neuropsychopharmacol Biol Psychiatry. 2010 Jun. 23.

SUMMARY OF THE INVENTION

Described herein are methods for enhancing or inhibiting (or a combination of both) susceptibility of a tissue (and particularly brain tissue) to pharmacological (drug) and/or radiation treatment by applying magnetic stimulation to up-regulate or down-regulate activity of one or more target tissue regions.

As described herein, magnetic stimulation, including transcranial magnetic stimulation (TMS), is applied used to alter the blood flow and metabolic rate of a portion of the body. In one embodiment, the diseased portion of the body slated for radiation or pharmacotherapy is up-regulated such that blood perfusion and metabolic rate of that tissue are increased thereby sensitizing this area to the effects of radiation and of drugs. In another embodiment, non-diseased portions of the body are down-regulated such that blood perfusion and metabolic rate of that tissue are decreased, thereby helping to protect those portions of the body from the effects of radiation and of drugs. In another embodiment, tissue that has been damaged from the effects of radiation and/or drugs may be up-regulated such that increased blood perfusion and metabolism may help with the cellular and tissue repair process.

BRIEF DESCRIPTION OF THE DRAWINGS

FIG. 1 illustrates one example of treatment of a target tissue (in this example, brain tissue) using magnetic stimulation to alter the susceptibility of the tissue to treatment by a drug or radiotherapy.

DETAILED DESCRIPTION OF THE INVENTION

Included are systems and methods for modulating the susceptibility of one or more tissue regions to a pharmacological and/or radiation therapy. In general, a target tissue region may be made more susceptible to a pharmacological and/or radiation treatment by up-regulating the region through the application of magnetic energy. Similarly non-target tissue regions may be made less susceptible to a pharmacological and/or radiation therapy by down-regulating the region through the application of magnetic energy. The orientation and/or frequency of applied magnetic energy may result in selectively up-regulating and/or down regulating metabolic activity.

For example, transcranial magnetic stimulation (TMS) is known to modulate metabolic activity in targeted brain regions, which may be visualized using scanning techniques such as PET scans. There is a widespread belief that low-frequency stimulation of target brain regions causes down-regulation (e.g., inhibition) of the target brain regions, while up-regulation may be achieved using high-frequency (e.g., greater than 5 Hz) stimulation. Work in our lab has suggested that the orientation of the applied TMS may also contribute to determine if a region is up-regulated or down-regulated; in particular, preliminary studies suggest methods of achieving low-frequency TMS (e.g., less than 3 Hz) that results in up-regulation of target brain regions, particularly when the TMS coil(s) are oriented so that the induced current or the principle current at the apex of the TMS electromagnet is oriented transversely to the AP axis of a subject's head (e.g., the AP axis of the head, skull, brain, etc.).

In particular, described herein are methods of performing TMS at to up-regulate or down-regulate target regions (e.g., a target brain region) and thereby modulate the sensitivity of the target region to a therapy such as a pharmacological, immunological, or radiation therapy.

As used herein, low-frequency TMS may be used synonymously with slow rate or slow rTMS pulse rates, and may be between about 0.5 Hz to about 3 Hz. This low-frequency or slow rate rTMS pulse rates may be contrasted to traditionally "fast" rTMS pulse rates (e.g., between about 5-50 Hz). Thus, in some variations, low-frequency TMS may be less than about 5 Hz. As mentioned, low-frequency TMS is widely believed to result in inhibition of the target region, while high-frequency TMS is thought to result in up-regulation of the target region.

FIG. 1 illustrates one example of a method and system for modulating the susceptibility of a brain region to a pharmacological, immunological or radiation therapy. In FIG. 1, a target region 110 of a brain 100 is up-regulated with magnetic stimulation to increase the radio sensitivity of the tissue. Non-target regions 111 may be down-regulated by the selective application of TMS. In this example, a magnetic coil 120 is used to apply a magnetic stimulation process 121, immediately before, during or shortly after application of a drug 130 (e.g., using a drug delivery process 131 such as injection, oral, transcutaneous, etc.) and/or radiation treatment using a radiation treatment device 140 and an appropriate radiation delivery process 141. Thus a disorder may be treated by the overlapping application of a treatment modality (e.g., pharmacological treatment) with a magnetic stimulation that modulates the activity.

In some variations, the targeted tissue region is modulated simultaneous with the application of drug/immune agent/radiation, so that the applied magnetic field up- or down-regulates activity of the region resulting in a change in the perfusion rate of the target tissue and therefore either inhibiting or enhancing the susceptibility of the target region.

In another example, non-target brain regions may be made less sensitive to treatment (e.g., drug/radiation treatment) by magnetic stimulation. For example, down regulation of a targeted area by magnetic stimulation may be used to decreases radio-sensitivity of tissue. In some variation a target brain region may be up-regulated to enhance susceptibility to treatment while at the same time adjacent non-target brain regions may be made less sensitive by down-regulation. For example, a plurality of TMS coils may be used at different orientations and frequencies of stimulation to up-regulate some brain regions and to down-regulate others.

In one variation, magnetic stimulation may be used to improve tissue recovery at non-target region. For example, up-regulation of targeted areas by magnetic stimulation may increase blood flow and metabolic rate, thereby speeding healing processes. This may be performed in conjunction with the application of one or more drugs, compounds, therapeutic substances or the like, which may further enhance healing.

In some variations, magnetic stimulation may be applied to body region to increase drug availability at the target regions by increasing blood perfusion of that region, as mentioned above. Up-regulation of targeted area may increase local drug availability, aiding in targeting of the drug uptake and/or effect. Magnetic stimulation of a targeted tissue region may also decrease the availability of the drug at non-target regions by decreasing perfusion in these non-target regions. Down-regulation of non-targeted areas may lower local drug availability.

Although the examples provided herein describe primarily the use of magnetic energy (e.g., magnetic stimulation) to increase or decrease the susceptibility of tissue to a treatment such as drug, immuno-agent or radiation, any appropriate energy modality may be used. In particular, non-contact energy modalities may be used such as microwave, ultrasound, or the like. Further, the target tissue may be any appropriate tissue, and may not be limited to brain tissue or brain regions.

The various embodiments described above are provided by way of illustration only and should not be construed to limit the invention. Based on the above discussion and illustrations, those skilled in the art will readily recognize that various modifications and changes may be made to the present invention without strictly following the exemplary embodiments and applications illustrated and described herein. Such modifications and changes do not depart from the true spirit and scope of the present invention.

What is claimed is:

1. A method of increasing the effect of a drug upon a targeted area of a patient's tissue by transcranial magnetic stimulation (TMS), the method comprising:

delivering a drug that reaches a target tissue via blood vessels to the patient;

steering a TMS electromagnet to deliver a first magnetic field energy to the target tissue, wherein the first magnetic field energy has a low frequency of 5 Hz or less, wherein the TMS electromagnet is oriented so that an induced current in the target tissue or a principle current at an apex of the TMS electromagnet is oriented transversely to an anterior to posterior (AP) axis of the patient's head; and applying the first magnetic field energy to increase perfusion of the target tissue, so that availability of drug to the target tissue is increased.

2. The method of claim 1, further comprising applying a second magnetic field energy to a non-target tissue to decrease perfusion of the non-target tissue, so that availability of the drug to the non-target tissue is reduced.

3. The method of claim 1, wherein steering the TMS electromagnet further comprises steering a plurality of TMS coils to deliver the first magnetic field energy to the target tissue.

4. The method of claim 1, wherein applying the first magnetic energy further comprises applying the first magnetic energy at a low frequency between 0.5 Hz to 3 Hz.

5. The method of claim 1, wherein the target tissue is a deep brain tissue region.

6. The method of claim 1, wherein applying the first magnetic field energy is performed simultaneously with delivering the drug.

7. A method for increasing the effect of a drug upon a targeted area of a patient's tissue by transcranial magnetic stimulation (TMS), the method comprising:

delivering a drug that reaches a target tissue via blood vessels to the patient;

steering a TMS electromagnet to deliver a first magnetic field energy to the target tissue;

applying the first magnetic field energy to the target tissue to increase perfusion of the target tissue, so that availability of the drug to the target tissues is increased; and applying a second magnetic field energy to a non-target tissue to decrease perfusion of the non-target tissue, so that availability of the drug to the non-target tissue is reduced, wherein the first magnetic field energy has a low frequency of 5 Hz or less, wherein the TMS electromagnet is oriented so that an induced current from the TMS electromagnet is oriented transversely to an anterior to posterior (AP) axis of the patient's head.

8. The method of claim 7, wherein steering the TMS electromagnet further comprises steering a plurality of TMS coils to deliver the first magnetic field energy to the target tissue.

9. The method of claim 7, wherein the target tissue is a deep brain tissue region.

10. The method of claim 7, wherein applying the first magnetic field energy is performed simultaneously with delivering the drug.

11. A method of increasing the effect of a drug upon a targeted area of a patient's head by transcranial magnetic stimulation (TMS), the method comprising:

delivering a drug that reaches a target tissue via blood vessels to the patient;

steering a plurality of TMS electromagnets to deliver a first magnetic field energy to the target tissue, wherein the first magnetic field energy has a low frequency of 5 Hz or less, wherein the TMS electromagnet is oriented so that an induced current in the target tissue or a principle current at an apex of at least one of the TMS electromagnets is oriented transversely to an anterior to posterior (AP) axis of the patient's head; and applying the first magnetic field energy to increase perfusion of the target tissue, so that availability of drug to the target tissue is increased.

12. A method of increasing the effect of a drug upon a targeted area of a patient's tissue by transcranial magnetic stimulation (TMS), the method comprising:

delivering a drug that reaches a target tissue via blood vessels to the patient;

steering a TMS electromagnet to deliver a first magnetic field energy to the target tissue, wherein the first magnetic field energy has a low frequency of 5 Hz or less, wherein the TMS electromagnet is oriented so that a current induced from the TMS electromagnet is oriented transversely to an anterior to posterior (AP) axis of the patient's head; and applying the first magnetic field energy to increase perfusion of the target tissue, so that availability of drug to the target tissue is increased.

13. The method of claim 12, further comprising applying a second magnetic field energy to a non-target tissue to decrease perfusion of the non-target tissue, so that availability of the drug to the non-target tissue is reduced.

14. The method of claim 12, wherein steering the TMS electromagnet further comprises steering a plurality of TMS coils to deliver the first magnetic field energy to the target tissue.

15. The method of claim 12, wherein applying the first magnetic energy further comprises applying the first magnetic energy at a low frequency between 0.5 Hz to 3 Hz.

16. The method of claim 12, wherein the target tissue is a deep brain tissue region.

17. The method of claim 12, wherein applying the first magnetic field energy is performed simultaneously with delivering the drug.

* * * * *